United States Patent [19]
Harosi

[11] Patent Number: 5,671,737
[45] Date of Patent: Sep. 30, 1997

[54] SELF-OPERABLE TONOMETER FOR MEASURING INTRAOCULAR PRESSURE OF A PATIENT'S EYE

[75] Inventor: Ferenc I. Harosi, Falmouth, Mass.

[73] Assignee: Marine Biological Laboratory, Woods Hole, Mass.

[21] Appl. No.: 569,666

[22] Filed: Dec. 8, 1995

[51] Int. Cl.$^6$ ................................................ A61B 3/016
[52] U.S. Cl. ................................ 128/645; 128/652
[58] Field of Search ................................ 128/645, 650, 128/651, 652; 73/81

[56] References Cited

U.S. PATENT DOCUMENTS

| | | |
|---|---|---|
| 3,070,997 | 1/1963 | Papritz et al. |
| 3,290,927 | 12/1966 | Gambs. |
| 3,934,462 | 1/1976 | Rende ................ 73/80 |
| 4,508,121 | 4/1985 | Myers ................ 128/639 |
| 4,523,597 | 6/1985 | Sawa et al. ................ 128/652 |
| 4,558,707 | 12/1985 | Miyamae et al. ................ 128/680 |
| 4,759,370 | 7/1988 | Kozin et al. ................ 128/645 |
| 4,817,620 | 4/1989 | Katsuragi et al. ................ 128/648 |
| 4,860,755 | 8/1989 | Erath ................ 128/645 |
| 4,944,303 | 7/1990 | Katsuragi ................ 128/648 |
| 4,987,899 | 1/1991 | Brown ................ 128/645 |
| 5,033,841 | 7/1991 | Nishio et al. ................ 351/212 |
| 5,056,522 | 10/1991 | Matsumura et al. ................ 128/645 |
| 5,174,292 | 12/1992 | Kursar ................ 128/645 |
| 5,190,042 | 3/1993 | Hock ................ 128/645 |
| 5,203,331 | 4/1993 | Draeger ................ 128/652 |
| 5,305,747 | 4/1994 | McNaughton et al. ................ 128/652 |
| 5,363,155 | 11/1994 | Urinowski et al. ................ 351/205 |

OTHER PUBLICATIONS

Zeimer et al., "An Instrument for Self-Measurement of Intraocular Pressure," IEEE Transactions on Biomedical Eng., vol. BME-29, No. 3, 1982.

*Primary Examiner*—Jennifer Bahr
*Assistant Examiner*—Bryan K. Yarnell
*Attorney, Agent, or Firm*—Hale and Dorr LLP

[57] ABSTRACT

A tonometer for measuring intraocular pressure (IOP) allows a user to self-operably apply a removable, lightweight, ocular probe to gently flatten an area of the corneal surface. A transducer having a flexible springboard connected to the probe and serving as a plate of a variable capacitor is used to sense forces produced when the probe contacts the eye elastically deforming the springboard. The applanation area is detected with a video camera connected to a central processing unit (CPU) programmed to perform image analysis. The CPU uses multiple force and multiple area values determined in rapid succession so that force and applanation area data are closely related in time. Linear regression analysis is used on data pairs to determine an average value for IOP in only about 1–2 seconds. The probe has a clear window with markings for delimiting a calibration area. The slight passive movements of the probe in this process are frictionless and cause no error in force determination. The IOP determination is independent of gravity and thus may be carried out in any orientation as well as under the condition of weightlessness.

19 Claims, 2 Drawing Sheets

SELF-OPERABLE TONOMETER FOR MEASURING INTRAOCULAR PRESSURE OF A PATIENT'S EYE

FIELD OF THE INVENTION

This invention relates to a method and apparatus for determining intraocular pressure (IOP) of a patient's eye.

BACKGROUND OF THE INVENTION

The human eye has a cornea that covers an anterior chamber filled with a watery fluid known as the aqueous humor. The cornea, which is soft and flexible, derives its firmness from the hydrodynamic intraocular pressure (IOP) generated by the aqueous humor. IOP is measured with a tonometer, a device that is particularly useful for detecting glaucoma, an ocular abnormality characterized by elevated levels of IOP and which, if unchecked, can lead to blindness.

To make these measurements, tonometers typically rely on the property of elastic bodies that an applied force to the body and a resulting deformation due to the applied force are directly proportional. Consequently, when force is applied over a known area of contact, a pressure value can be determined. This determination is made by some tonometers by applying a flat solid surface against the cornea. The flattening of the cornea in this manner is the applanation method. Other tonometers may use a non-contacting method in which a puff of air is directed at the eye. Devices based on this non-contacting method are believed to be less accurate than the applanation type tonometers.

A tonometer that uses applanation is described in Papritz, U.S. Pat. No. 3,070,997. That device has a solid and transparent probe that is pressed against the corneal surface with a force applied by a spring-loaded mechanical balance. When the probe flattens the corneal surface, the applied pressure is balanced primarily by the IOP (while there are other factors, they are typically negligible). A practitioner looks at the patient's eye through a telescope and controls the applied force until the probe causes a corneal applanation with a diameter of exactly 3.06 mm. Although two special prisms built into the probe help the practitioner detect the desired area of contact, the method is subjective and its accuracy depends on the practitioner's skill. When the diameter of applanation is 3.06 mm, the applied force bears a simple relationship to the IOP measured in mm Hg, which can be read from a dial.

Various other applanation tonometers have been developed. In Draeger, U.S. Pat. No. 5,203,331, a measuring body with a flat transparent surface is moved toward the eye with a linear motor. An infrared LED and a photodiode are positioned at the back of the measuring body for detecting internally reflected light. When the measuring body contacts the eye, the contact area reduces the amount of light internally reflected, and thus the detector's signal is proportional to the area of contact between the cornea and the measuring body. When the signal corresponds to 3.06 mm applanation, the instantaneous force of the linear motor is determined.

In Draeger, therefore, measurement of IOP depends on the sensitivity of the linear motor and on the detection of a specific area of applanation. In addition, the measuring body appears to be difficult to manufacture and it appears to be difficult to align all of the components.

In Matsumura, U.S. Pat. No. 5,056,522, a device measures both eye access length and eye pressure. As shown in FIGS. 12-14, a probe that deforms the corneal surface is coupled to a spring. The force of the probe is determined with a needle and a scale. Light reflected from the surface of the eye is used to determine the area flattened by the probe. When the applanation reaches a predetermined value, (when the diameter is 3.06 mm) the force measured by the needle and scale is used to determine the pressure. In such a device, the sensitivity of the spring could be a problem. Moreover, detecting area from the side raises concerns about accuracy.

SUMMARY OF THE INVENTION

A tonometer according to the present invention has a number of features that improve on aspects of these prior tonometers. The tonometer of the present invention allows a user to self-operably measure IOP accurately and repeatable with a plurality of force and area measurements. These measurements are made with a probe that is easily removable for cleaning or is disposable.

The probe is moved into contact with the eye manually (although the mechanism could be automated with stepping motors), and the force between the cornea and the probe is sensed with a transducer that preferably includes circuitry with a variable capacitor, a frequency divider, and a period counter for converting the force into a digital signal. The area of applanation is detected optically, preferably with a video camera, such as a two-dimensional charge coupled device (CCD), which senses light reflected from the cornea through a window in the probe, and provides signals indicating the applanation area to a central processing unit (CPU). The CPU receives at least two samples for the force and the area of applanation, and determines IOP, preferably by performing image analysis on data from the camera, and linear regression analysis on the force and area measurements.

The force and area samples are correlated in time and are provided as data pairs that can be displayed on a video monitor as a two-dimensional plot. The CPU calculates the IOP in terms of mm Hg, and can cause the result to be displayed on a video monitor and/or announced over a speaking device with a synthesized voice.

The probe is held so that it is manually removable and replaceable. This holding arrangement allows the probe to be cleaned easily; indeed, the probe can be kept in a cleaning solution when not in use, or it can be disposable. The probe is preferably held with a split ring against a platform that has an opening axially centered with respect to the probe for allowing the passage of light. The front end of the probe has a window with a known area delimited for calibration.

The tonometer of the present invention takes advantage of the speed and accuracy of digital computer technology, and provides automated determinations of IOP rapidly and accurately regardless of the operator's skills. The tonometer is self-operable, self-contained, readily portable, and does not require any significant skill or assistance of another person. Because a plurality of data sets are sampled rapidly and frequently and are obtained during the course of the brief contact between the probe and the cornea, IOP is determined not at any one particular area of deformation, but rather within an acceptable range of applanations, thus promoting speed and accuracy. The probe is preferably easily manually removable and reattachable for cleaning and/or replacement, thus reducing the risk of infection. The design is not overly complicated, and therefore can be manufactured without undue expense. Other features and advantages will be apparent from the following detailed description, claims, and drawings.

DETAILED DESCRIPTION

Figure 1:
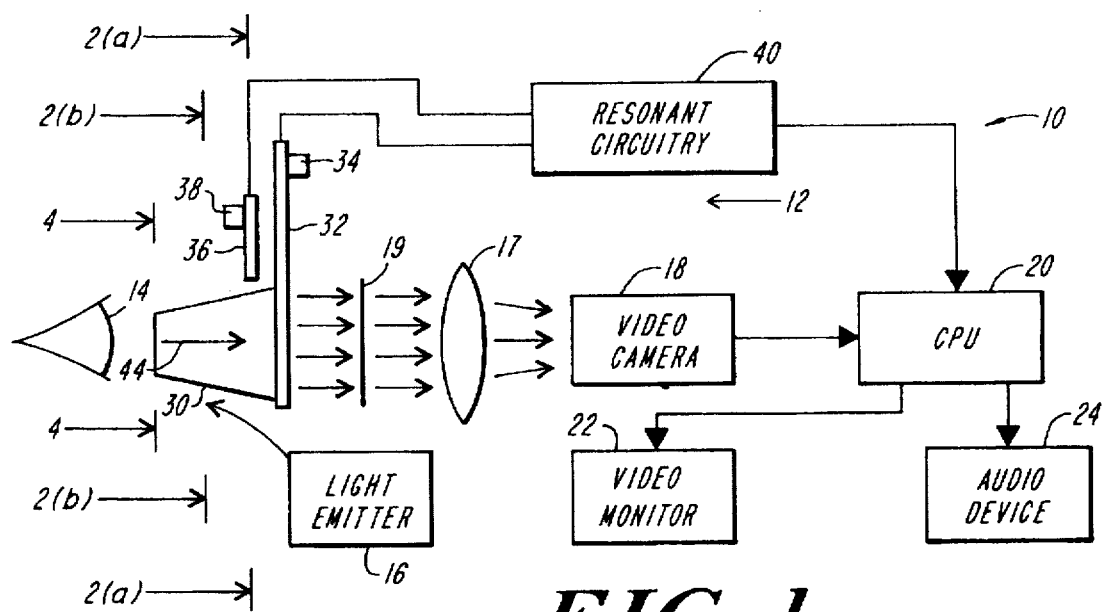
FIG. 1 is a pictorial block diagram of a tonometer according to the present invention.

FIG. 1 provides an overview of the tonometer according to the present invention. A self-operable tonometer 10 has an ocular probe 30 with a flat, transparent window. The tonometer is manipulated by a user so that the probe contacts and deforms an area of a cornea 14. The force of this contact is measured with a force transducer 12 that provides digital signals that represent the force between probe 30 and cornea 14.

An optical system measures the area deformed by the probe, and a processing system determines IOP in response to the force and area measurements. The area of applanation is sensed by an optical system that preferably includes at least two light emitters 16 (only one of which is shown) on opposite sides of probe 30 for providing light adjacent to probe 30. Light reflected from the cornea and passes through a probe window at the end of the probe. This reflected light is filtered with filter 19 to remove visible ambient light and to pass the infrared wavelengths provided by light emitters 16. The filter is preferably a thin gelatin filter, such as that known as a WRATTEN No. 87 produced by Kodak. The filtered light is focused with appropriate optics, represented by lens 17, to form real images of the probe window and to project these images onto the light-sensitive elements of a video camera 18, preferably a two-dimensional CCD array. Video camera 18 provides to CPU 20 digital data representing video images of the area of contact between probe window and cornea.

A central processor unit (CPU) 20 receives in rapid succession signals alternating between force transducer 12 and the video camera 18 (via a frame-grabbing board that is part of the CPU). These signals are processed to provide force/applanation-area data pairs. Using a plural number of these data pairs sampled rapidly and frequently, data is transferred to and stacked in a memory buffer, from which the CPU performs analysis to determine IOP and to convert it to a whole natural number in terms of mm Hg. CPU 20 can then cause a visual display of the results on a video monitor 22 positioned to be seen by the user during the test, preferably by mounting it so that it can easily be moved to be seen by the eye that is not being tested. The CPU can also cause an audio device 24 to announce the whole number with a speech synthesizer (in any desired language). The video monitor thus provides visual feedback to the user for making contact with the eye for applanation. The total time for this process is preferably only about 1–2 seconds.

The method and apparatus for measuring the force of contact are described in more detail with additional reference to FIGS. 2(a), 2(b), 3, and 5. Transducer 12 senses changes in the probe's position with a springboard 32 and a stationary plate 36 which serve as first and second plates of a variable capacitor. Springboard 32 has a free lower end connected to a probe platform 33, and an upper end rigidly connected to a first electrically insulating rod 34. Stationary plate 36 is rigidly connected to a second electrically insulating rod 38 and is positioned to be substantially parallel to and to form a narrow gap with springboard 32. Springboard 32 has slits 42 extending inwardly and horizontally from opposite sides below rod 34 to obtain a desired stiffness with which springboard 32 bends pivotally relative to first rod 34. At the top of springboard 32 and plate 36 are contact tabs 43 and 48, respectively, by which springboard 32 and plate 36 are coupled to resonant circuitry 40. Plate 36, at its bottom end, has a rectangular cutout region 46 that accommodates receptacle 44 without interfering with movement of the plate.

In an exemplary embodiment, springboard 32 and plate 36 are preferably made of stainless steel, and each is about 0.005 inches thick. The inside surfaces of 32 and 36 (i.e., the surfaces that face one another) are coated with electrical insulation (not shown), such as transparent tape, to prevent electrical shorting between them. Excluding the contact tabs, springboard 32 and plate 36 are about 38 mm and 25 mm long, respectively, and each is about 26 mm wide. The center-to-center separations of rods 34 and 38 are about 10–11 mm vertically, and about 7 mm horizontally.

Probe platform 33 has a receptacle 44 with a split ring for holding probe 30. Centered in the split ring is an opening 45 in platform 33 for allowing the passage of light. By using such a split ring the probe is easily manually removable from the transducer's receptacle for cleaning, and is easily reattachable. Consequently, the probe can be kept in a cleaning solution or can be disposable.

The movable springboard in the variable capacitor allows measurements to be taken quickly, and also allows for a quick frictionless return when the probe is unloaded, i.e., when the probe is moved out of contact with the eye. Because the transducer measures passively with the elasticity of stainless steel and is not dependent on a motor or some other active, force-providing mechanism, factors relating to the operation of a motor need not be considered.

Figure 2A:
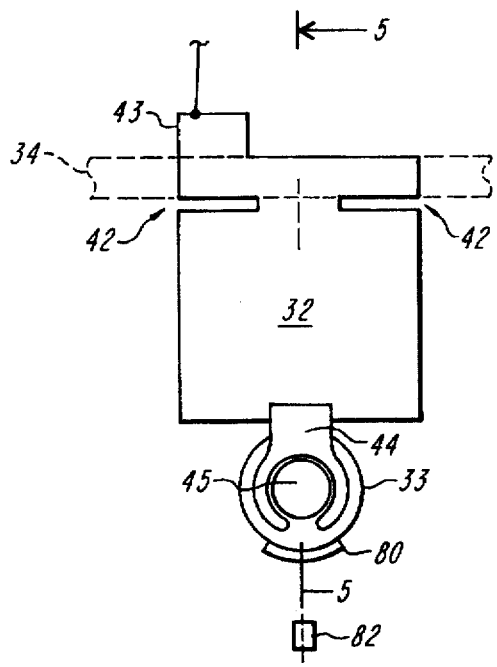
FIG. 2(a) and 2(b) are end views shown at lines 2(a)–2(a) and 2(b)–2(b) of FIG. 1, illustrating a movable plate and a stationary plate, respectively.
Figure 2B:
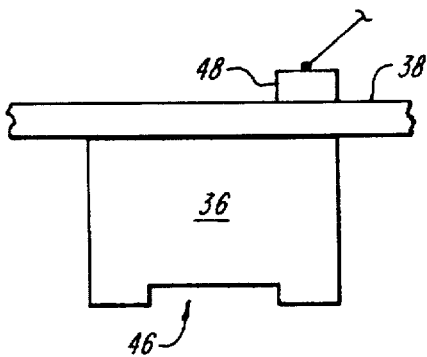
Figure 5:
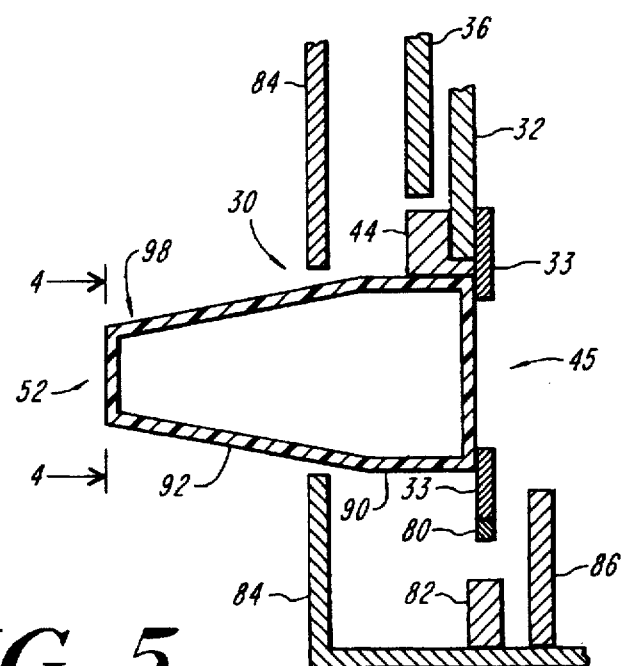
FIG. 5 is a cross-sectional view of the probe coupled to the transducer taken through section lines 5—5 of FIG. 2.

As shown in FIGS. 2(a) and 5, to reduce vibrations of springboard 32 due to its stored elastic energy when unloaded, springboard 32 is damped magnetically with a short piece of magnetic wire 80 glued to the lower edge of platform 33, and a strong permanent magnet 82 below probe 30. Magnet 82 is affixed to housing 84 so that the distance between a selected pole of magnet 82 and magnetic wire 80 can be adjusted. Magnet 82 and wire 80 thus help eliminate free vibrations. Alternatively, damping can be accomplished by using a piece of nonmagnetic, electrical conductor, such as brass, in place of wire 80, forming a narrow air-gap to magnet 82. This arrangement can produce dragging force to movement by eddy currents.

Also mounted to a base of housing 84 is a mechanical stop 86 that limits rearward movement of platform 33, and hence springboard 32.

Figure 3:
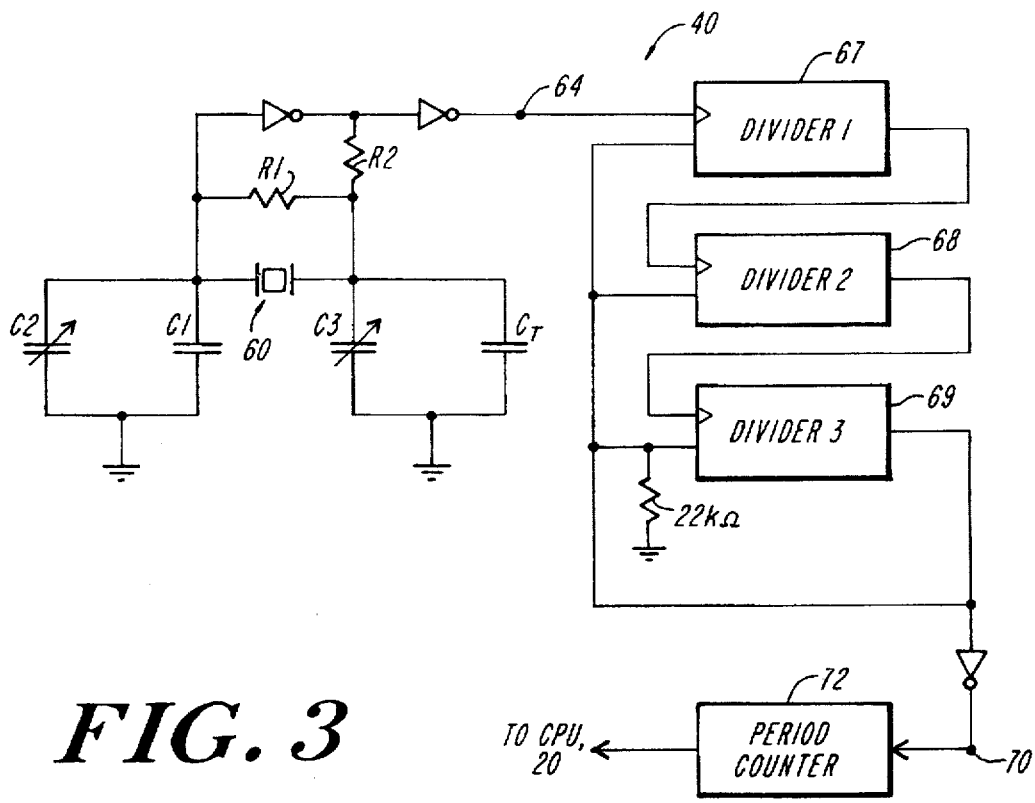
FIG. 3 is a partial schematic, partial block diagram of a circuitry in a force transducer.

Referring particularly to the schematic of FIG. 3, the variable capacitor formed by springboard 32 and plate 36 is represented as capacitor $C_T$ and is coupled to oscillator circuit 40. Circuit 40 has a high frequency quartz crystal 60, such as a MATTCO crystal, having a nominal frequency of about 7.89 Mhz. Crystal 60 is part of a resonant circuit that includes a fixed capacitor C1 with capacitance of 20 pF; adjustable trimming capacitors C2 and C3 with capacitances ranging from 16–60 pF and 5.5–18 pF, respectively; variable capacitor $C_T$ that ranges approximately from 5–15 pF; resistor R1 with resistance of 10 Mohms; R2 with resistance of about 52 Kohms; and an inverting buffer amplifier. When springboard 32 moves, the force directed along arrow 44 (FIG. 2) changes capacitance $C_T$, thus causing a measurable change in the frequency of the pulses provided at output 64.

These pulses are provided as clock pulses to a first of three cascaded frequency dividers 67, 68, 69. First frequency divider 67 receives the pulses and divides down by $2^{14}$. The pulses from divider 67 provide clock pulses to second frequency divider 68, which divides down by $2^5$, and the output pulses from divider 68 are provided to third frequency divider 69 which divides down by a factor of 3. The resulting pulses are thus divided down by $3 \times 2^{19}$, which is about $1.57 \times 10^6$. Based on the nominal frequency of crystal 60, the nominal frequency of the pulses at output node 70 of divider 69 is about 5 hz, and hence the period is about 200 ms. These pulses are then used as gating pulses between a higher frequency oscillator and a 16-bit binary counter whose output is transferred to the CPU 20 (FIG. 1). Period counter 72 can be similar to a circuit described in Horowitz and Hill, *The Art of Electronics*, 1980, pp. 619–20.

The probe and the measurement of the area of applanation when the probe contacts the eye are described in more detail in connection with FIGS. 4 and 5. An exemplary probe with overall length of about 26 mm is made of a rigid, translucent polycarbonate and has three integral portions. A larger diameter cylindrical end 90 has an outer diameter of about 12.6 mm, and a length of about 4 mm. Cylindrical end 90 is gripped by the split ring with a compressive force. To assist in this gripping, the outside surface of end 90 can be roughened. Cylindrical end 90 is shown sealed closed at the end that faces platform 33, but it can be open. A closed probe is preferred, however, to prevent contamination of the probe's inside surfaces. At end 90 is opening 45 in platform 33, axially centered with respect to probe 30, for allowing light to pass to the filter and other optics (see also FIGS. 1 and 2).

An integral frustro-conical portion 92 has an axial length of about 22 mm and tapers from cylindrical end 90 to a front window 52 which has an outer diameter of about 7 mm. A front portion 98 is preferably machined to roughen the surface to enhance light scattering from outside to the inside. Window 52 of probe 30 should be thin (e.g., about 0.1 mm) to avoid parallax error that could otherwise occur during applanation, but stiff enough to prevent its own deformation. Middle portion 92 is about 15 mm long and is preferably stained on its sides to make it non-transparent, e.g., with carbon deposit, and/or polished to be more reflective. Because filter 19 is used to block ambient light, this non-transparency requirement is not critical for proper operation.

Figure 4:
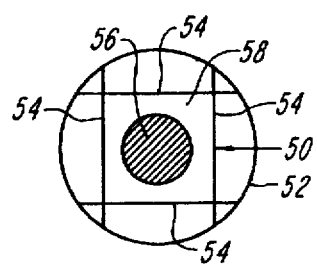
FIG. 4 is a front view shown at lines 4—4 in FIGS. 1 and 5, illustrating a window of the probe with four lines inscribed on it, to delimit a known area for calibration.

Referring particularly to FIG. 4, the circular outer surface of probe window 52 contacts the cornea. Centered in this window is a hairline calibration area delimited by four thin lines 54 scored on the inside surface of window 52. Lines 54 are preferably stained to provide good contrast. The contacting surface should be sufficiently smooth to make comfortable contact with the cornea, and it can be appropriately coated to control surface tension.

Referring also to FIG. 1, light emitter 16, preferably an infrared LED, directs light toward the eye, preferably on at least two sides of the probe. As the probe approaches the eye along its optic axis, more and more reflected light arrives at window 52 until contact is made with the cornea, at which time the contact area appears as a darker disk. This disk is sensed with video camera 18, which provides images to a frame grabbing board of CPU 20 at a rate of about 30 frames per second. CPU 20 uses a digital processing algorithm with contrast enhancement to determine the area of applanation by comparing a darkened area 56 and the area 58 enclosed by the calibration square (see FIG. 4). The comparison of flattened area 56 and area 58 in the calibration square is preferably made simply by counting darkened pixels within each of the boundaries. Depending on the optical magnification, hundreds of pixels may correspond to each square millimeter and thus high accuracy can be obtained. Because the clear window of the probe is about 7 mm in diameter and the square is 4 mm to a side, the circular area of applanation from the range of 2–5 mm in diameter can be distinguished from the straight-edged calibration square with great certainty and the ratio of the two areas can be determined accurately.

CPU 20 thus receives digital counts from force transducer 12 at a rate of about 5 per second, and video image signals from video camera 18 at a rate of about 30 per second. The CPU synchronizes the data so that the force values are associated with corresponding areas of contact value. The CPU can use a single data pair, but preferably the CPU uses a number of data pairs that give points on a sensed force versus the area of corneal applanation, and uses appropriate algorithms that perform linear regression analysis. From this relationship, the CPU determines an average value for IOP.

The CPU converts the determined average IOP into a numerical value in terms of mm Hg. For example, pressures ranging 0.136 g/mm$^2$ to 0.272 g/mm$^2$ correspond to a range of about 10–20 mm Hg. These are common and normal values of IOP. The tonometer of the present invention can also detect much smaller pressures or pressures well beyond this range, depending on its construction and calibration. The CPU then causes the numerical value of the IOP to be displayed on video monitor 22 and to be announced by audio device 24, such as a speaker, with a synthesized voice that can provide the measurement in a desired one of a number of languages. If the contact between the probe and cornea was inadequate to allow successful determination, an audible beep is sounded to indicate that the test should be repeated.

When the tonometer is first turned on, CPU 20 goes into a software loop in which the CPU takes samples from the force transducer by interrupt when a count is available. The rest of the time, the CPU is transferring video frames and analyzing the video image data. Data for force and area are stacked in a buffer. Before the first contact, data corresponding to zero force and zero area are determined, and/or the tonometer can be calibrated as noted below.

When contact is made with the patient's eye, the following criteria are checked: (1) the contact area should be circular within a certain degree of ellipticity; and (2) the diameter of applanation should be within a range of about 2.5 to 4.5 mm. A minimum of two data pairs are then compared with pre-contact values and used to determine IOP.

The video monitor need not have high resolution or be large in size. A monochromatic liquid crystal display with a screen of about 3×4 inches is sufficient. This monitor may also be fabricated like the viewers on some hand-held video recording cameras, that permit replay and viewing of recorded video frames. The monitor thus provides visual feedback to the user; aids the user in programming, testing, and calibration; and displays the outcome of determined IOP values in addition to voice announcements. After a preset time period (e.g., about 5 second) elapses, the tonometer resets itself, and is ready for a next determination. The result can be stored in the computer, if desired, or printed out individually as well as in tabulated listings.

Housing 84 is preferably a rectangular box that encloses at least transducer 12, circuitry 40, and light emitter(s) 16; the box preferably also houses filter 19, optics (represented by lens 17), and video camera 18. If permitted by miniturization, the housing preferably also encloses CPU 20, audio device 24, and has video monitor 22 mounted as a movable attachment. The box that forms the housing is preferably hand-holdable in size.

The tonometer is preferably used with a mechanical manipulator (not shown) that allows the user to move probe 30 into contact with the cornea. A head-piece and a chin-rest, which are generally known in the field of ocular testing and evaluation, are provided for the user to position his or her head. The housing is mounted to the manipulator, which has course and fine adjustments for positioning and moving the housing (with the probe) along three mutually orthogonal axes. With these course and fine adjustments, this mechanism enables the operator to position the probe in line with the tested eye and then to make contact with the eye. The head-piece and chin-rest are constructed on a metal base, such as aluminum, for stability. When this manipulation is done, the user can use the video monitor to receive visual feedback of the contact area.

If the tonometer is positioned so that probe 30 points upwardly, the probe's weight acts as a force on springboard 32. Because gravitation is an accurately known force on earth, the device can be calibrated in this position by placing standard weights on probe 30. When the device is positioned for use, such that probe 30 assumes a horizontal position, horizontally acting forces are needed to bend springboard 32. Because elastic deformation is the measure of force, the device can operate accurately in any orientation, and even in weightlessness.

Having described embodiment of the present invention, it should be apparent that other modifications can be made without departing from the scope of the invention as defined by the appended claims. For example, while the circuitry has been described with particular frequencies and frequency dividers have been mentioned, other circuitry could be used, as long as it converts force to a digital signal. The processing has been described as being done by a CPU, but a less powerful or dedicated processor, such as an application-specific integrated circuit (ASIC), could be used.

What is claimed is:

1. A tonometer for measuring intraocular pressure (IOP) of a patient's eye, the tonometer comprising:
    a probe for contacting the eye, the probe being movable relative to the eye while in contact with the eye;
    a transducer coupled to the probe and including circuitry for providing a digital force signal indicating a force with which the probe contacts the eye, the transducer including a first movable plate coupled to the probe, and a second stationary plate separated from the first by a narrow gap and substantially parallel to the first movable plate, the first and second plates forming a variable capacitor;
    a light emitter for emitting light toward the eye;
    a camera for receiving light reflected from the eye and for providing a digital video image data indicating an area of applanation; and
    a processor for receiving digital force signals and digital video image data and for determining IOP in response thereto.

2. A tonometer for measuring intraocular pressure (IOP) of a patient's eye, the tonometer comprising:
    a probe for contacting the eye, the probe being movable relative to the eye while in contact with the eye, wherein the probe has a flat, transparent window with a known delimited calibration area such that a contact area between the probe and the eye can be compared to the calibration area to determine areas of applanation;
    a transducer coupled to the probe and including circuitry for providing a digital force signal indicating a force with which the probe contacts the eye;
    a light emitter for emitting light toward the eye;
    a camera for receiving light reflected from the eye and for providing a digital video image data indicating an area of applanation; and
    a processor for receiving digital force signals and digital video image data and for determining IOP in response thereto.

3. The tonometer of claim 2, wherein the probe is made of a lightweight firm plastic.

4. A tonometer for measuring intraocular pressure (IOP) of a patient's eye, the tonometer comprising:
    a probe for contacting the eye with a force and for deforming an area of the eye, the probe being movable relative to the eye when in contact with the eye so that the force and area can vary;
    a transducer coupled to the probe for providing force signals indicative of forces with which the probe contacts the eye;
    an optical detector for providing area signals indicative of areas of contact between the probe and the eye; and
    a processor, responsive to the force and area signals, for using a plurality of force and area signals to determine IOP, the processor receiving force signals at a first constant rate and area signals at a second constant rate different from the first constant rate, the processor synchronizing the force and area signals.

5. The tonometer of claim 4, the processor receiving at least a first set of signals representing a first force and a first corresponding deformed area, and a second set of signals including a second force different from the first force and a second corresponding deformed area, the processor determining the IOP based on at least the first and second sets of signals.

6. The tonometer of claim 4, the processor being programmed to perform linear regression on the plurality of force and area signals.

7. A method for measuring an intraocular pressure (IOP) of a patient's eye with a device including a probe for contacting the eye with a varying force and for deforming the eye with a varying area, a force sensor for determining forces with which the probe contacts the eye, and an area sensor for determining areas of flattening of a cornea of the patient's eye, the method comprising the computer-implemented steps of:
    measuring, at a first constant rate, a plurality of forces representing forces with which the probe contacts the eye;
    measuring, at a second constant rate different from the first rate, a plurality of areas representing areas of deformation of the eye when the probe contacts the eye; and
    determining a value of IOP based on a plurality of force signals and a plurality of area signals.

8. The method of claim 7, the determining step including performing a linear regression analysis.

9. The method of claim 7, the device having a springboard connected to the probe, wherein, prior to the measuring steps, the device is calibrated according to the following steps:
    changing the orientation of the device so that the springboard is deflected by gravity, and
    measuring the force while the springboard is deflected.

10. A tonometer for measuring intraocular pressure (IOP) of a patient's eye, the tonometer comprising:

a probe for contacting the eye;

a transducer, coupled to the probe in an easily removable and reattachable manner, for determining a force with which the probe contacts the patient's eye and for providing a force signal, the transducer including a stationary plate and a movable plate that form a variable capacitor, the probe being attached to the movable plate such that deflections of the movable plate causes changes in the capacitance of the variable capacitor;

an optical system for determining an area of applanation when the probe contacts the eye and for providing an area signal indicative of the area; and a processor for receiving the force signal and the area signal and for determining IOP in response thereto.

11. The tonometer of claim 10, the probe being held to the movable plate at least in part by a split ring.

12. The tonometer of claim 11, the movable plate including a platform coupled to the split ring and having an opening axially aligned with the probe for allowing light to pass to a detection portion of the optical system.

13. A tonometer for measuring intraocular pressure (IOP) of a patient's eye, the tonometer comprising:

a probe for contacting the eye, the probe being movable relative to the eye while in contact with the eye;

a transducer coupled to the probe, the transducer including a first movable plate coupled to the probe, and a second stationary plate substantially parallel to the first movable plate, the first and second plates forming a variable capacitor;

circuitry coupled to the transducer for providing a force signal indicating a force with which the probe contacts the eye;

a light emitter for emitting light toward the eye;

an optical detector for receiving light reflected from the eye and for providing area data indicating an area of applanation; and a processor for receiving the force signals and area data and for determining IOP in response thereto.

14. The tonometer of claim 13, wherein the circuitry includes a crystal oscillator operating nominally at a first frequency and coupled to the variable capacitor at a node, the variable capacitor causing signals at variable frequencies to be provided at the node as the capacitance of the variable capacitor changes.

15. The tonometer of claim 14, wherein the circuitry further includes at least one frequency divider coupled to the node for receiving the signals at variable frequencies and for producing a signal at lower variable frequencies, and a period counter for providing to the processor a digital signal indicative of these lower variable frequencies.

16. The tonometer of claim 13, further comprising a video monitor for receiving and displaying the video image data indicating the area of applanation, the monitor being positioned so that the monitor is visible to the patient during operation of the tonometer.

17. The tonometer of claim 16, the transducer for sensing force without a force-providing mechanism by converting movements of the probe into elastic deformations.

18. The tonometer of claim 16, further comprising an audio device for audibly announcing a value related to the IOP.

19. A tonometer for measuring intraocular pressure (IOP) of a patient's eye, the tonometer comprising:

a probe for contacting the eye, the probe being movable relative to the eye while in contact with the eye and having a transparent window with a known delimited calibration area such that a contact area between the probe and the eye can be compared to the calibration area to determine areas of applanation;

a transducer coupled to the probe;

circuitry coupled to the transducer for providing a force signal indicating a force with which the probe contacts the eye;

a light emitter for emitting light toward the eye;

an optical detector for receiving light reflected from the eye and for providing area data indicating an area of applanation; and a processor for receiving the force signals and the area data and for determining IOP in response thereto.

* * * * *